United States Patent
Tsuji et al.

(10) Patent No.: US 7,049,093 B2
(45) Date of Patent: May 23, 2006

(54) METHOD OF CLASSIFYING AND COUNTING NUCLEATED BONE MARROW CELLS

(75) Inventors: Tomohiro Tsuji, Hyogo (JP); Yusuke Mori, Hyogo (JP); Takashi Sakata, Hyogo (JP); Yukio Hamaguchi, Hyogo (JP)

(73) Assignee: Sysmex Corporation, Hyogo (JP)

( * ) Notice: Subject to any disclaimer, the term of this patent is extended or adjusted under 35 U.S.C. 154(b) by 310 days.

(21) Appl. No.: 09/992,221

(22) Filed: Nov. 6, 2001

(65) Prior Publication Data

US 2002/0086344 A1    Jul. 4, 2002

(30) Foreign Application Priority Data

Nov. 8, 2000    (JP)    ............................. 2000-341113

(51) Int. Cl.
*C12Q 1/06*    (2006.01)

(52) U.S. Cl. ........................ 435/39; 435/39; 435/7.24; 436/63; 436/172

(58) Field of Classification Search .................. 436/63, 436/10, 172, 164, 17; 435/6, 7.24, 34, 39
See application file for complete search history.

(56) References Cited

U.S. PATENT DOCUMENTS

| | | | | |
|---|---|---|---|---|
| 2,656,508 | A | * | 10/1953 | Coulter ....................... 324/71.1 |
| 4,284,412 | A | * | 8/1981 | Hansen et al. ............. 435/7.24 |
| 4,492,752 | A | * | 1/1985 | Hoffman et al. ........... 435/7.21 |
| 5,298,426 | A | * | 3/1994 | Inami et al. .................... 436/63 |
| 5,516,695 | A | * | 5/1996 | Kim et al. ..................... 436/17 |
| 5,559,037 | A | * | 9/1996 | Kim et al. ..................... 436/63 |
| 5,817,519 | A | * | 10/1998 | Zelmanovic et al. ......... 436/63 |

FOREIGN PATENT DOCUMENTS

EP    1 004 880    5/2000

OTHER PUBLICATIONS

Bentley et al., "Correction of Bone Marrow Nucleated Cell Counts for the Presence of Fat Particles" (Jul. 1995) American Journal Of Clinical Pathology, 104 (1) 60-4.*
Bentley et al, Am. J. Clin. Pathol., vol. 102. No. 2 pp. 223-230 (1994) (full document—Board decision cited abstract only).*
G. d'Onofrio, et al., "Automated Analysis of Bone Marrow: Routine Implementation and Differences from Peripheral Blood", Laboratory Hematology 4: 71-79.
G. Fan, et al., "Quantitative and Qualitative Bone Marrow Analysis Using the Abbott Cell-Dyn 4000 Hematology Analyzer", Laboratory Hematology 5:45-51.

* cited by examiner

*Primary Examiner*—Francisco Prats
(74) *Attorney, Agent, or Firm*—Cohen, Pontani, Lieberman & Pavane

(57) ABSTRACT

A method for classifying and counting nucleated bone marrow cells comprises the steps of: (1) mixing a sample of bone marrow fluid with an erythrocyte lysing agent to lyse erythrocytes in the sample and render leukocytic cells and erythroid cells in the sample suitable for staining, and staining the sample with a fluorescent dye for producing a difference in intensity of fluorescence between the leukocytic cells and the erythroid cells; (2) introducing the resulting sample to a flow cytometer to detect at least one kind of scattered light and at least one kind of fluorescence; (3) classifying and counting nucleated bone marrow cells, the leukocytic cells and the erythroid cells with use of a difference in the intensity of the fluorescence and the scattered light; (4) calculating the ratio of the nucleated bone marrow cells to the erythroid cells or leukocytic cells from the obtained erythroid cell count or leukocytic cell count and the obtained nucleated bone marrow cell count; and (5) calculating the ratio of the leukocytic cells to the erythroid cells from the erythroid cell count and the leukocytic cell count.

11 Claims, 4 Drawing Sheets

METHOD OF CLASSIFYING AND COUNTING NUCLEATED BONE MARROW CELLS

CROSS-REFERENCE TO RELATED APPLICATION

This application is related to Japanese Patent Application No. 2000-341113 filed on Nov. 8, 2000, whose priority is claimed under 35 USC §119, the disclosure of which is incorporated by reference in its entirety.

BACKGROUND OF THE INVENTION

1. Field of the Invention

The present invention relates to a method for classifying and counting nucleated bone marrow cells. More particularly, it relates to a method for classifying and counting nucleated bone marrow cells by means of flow cytometry.

2. Description of Related Art

In the field of clinical tests, the classifying and counting of nucleated bone marrow cells helps to obtain extremely useful information for diagnosing diseases. For Example, normal bone marrow commonly contains specific proportions of nucleated cells such as leukocytic cells, erythroid cells and the like. Some diseases cause changes in the number of nucleated cells, e.g., leukocytic cells, erythroid cells and the like, which results in changes in the proportions of leukocytic cells and erythroid cells. For example, acute leukemia of various types, myelodysplasia (MDS) and chronic myelogenous leukemia (CML) increase the number of nucleated cells, while anaplastic anemia and hypoplastic leukemia decrease the number of nucleated cells. Leukemia of various types and malignant lymphoma associated with abnormal hyperleukocytosis increase the number of leukocytic cells, and pure red cell anemia decreases the number of erythroid cells. Further, in the case of anemia, the number of erythroid cells increases. Thus, it is very useful for diagnosing diseases and determining the cell production ability of hematopoietic forming organs to classify and count nucleated bone marrow cells, e.g., leukocytic cells and erythroid cells in bone marrow and obtain their proportions.

Components contained in bone marrow have usually been classified and counted by producing smear samples of bone marrow, staining the samples with suitable dyes and microscopically observing the stained samples.

In recent years, whole blood classifying and counting apparatus are available which utilize the principle of flow cytometry. However, these apparatus involve such defects that lipid particles contained in bone marrow fluid disturb measurement and blood cells agglutinate easily. That makes difficult the accurate classification and counting of nucleated bone marrow cells.

SUMMARY OF THE INVENTION

The present invention provides a method for classifying and counting nucleated bone marrow cells including the steps of:

(1) mixing a sample of bone marrow fluid with an erythrocyte lysing agent to lyse erythrocytes in the sample and render leukocytic cells and erythroid cells suitable for staining, and staining the sample with a fluorescent dye for producing a difference in intensity of fluorescence between the leukocytic cells and the erythroid cells;

(2) introducing the resulting sample to a flow cytometer to detect at least one kind of scattered light and at least one kind of fluorescence;

(3) classifying and counting nucleated bone marrow cells, the leukocytic cells and the erythroid cells with use of a difference in the intensity of the fluorescence and the scattered light;

(4) calculating the ratio of the nucleated bone marrow cells to the erythroid cells or leukocytic cells from the obtained erythroid cell count or leukocytic cell count and the obtained nucleated bone marrow cell count; and (5) calculating the ratio of the leukocytic cells to the erythroid cells from the erythroid cell count and the leukocytic cell count.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
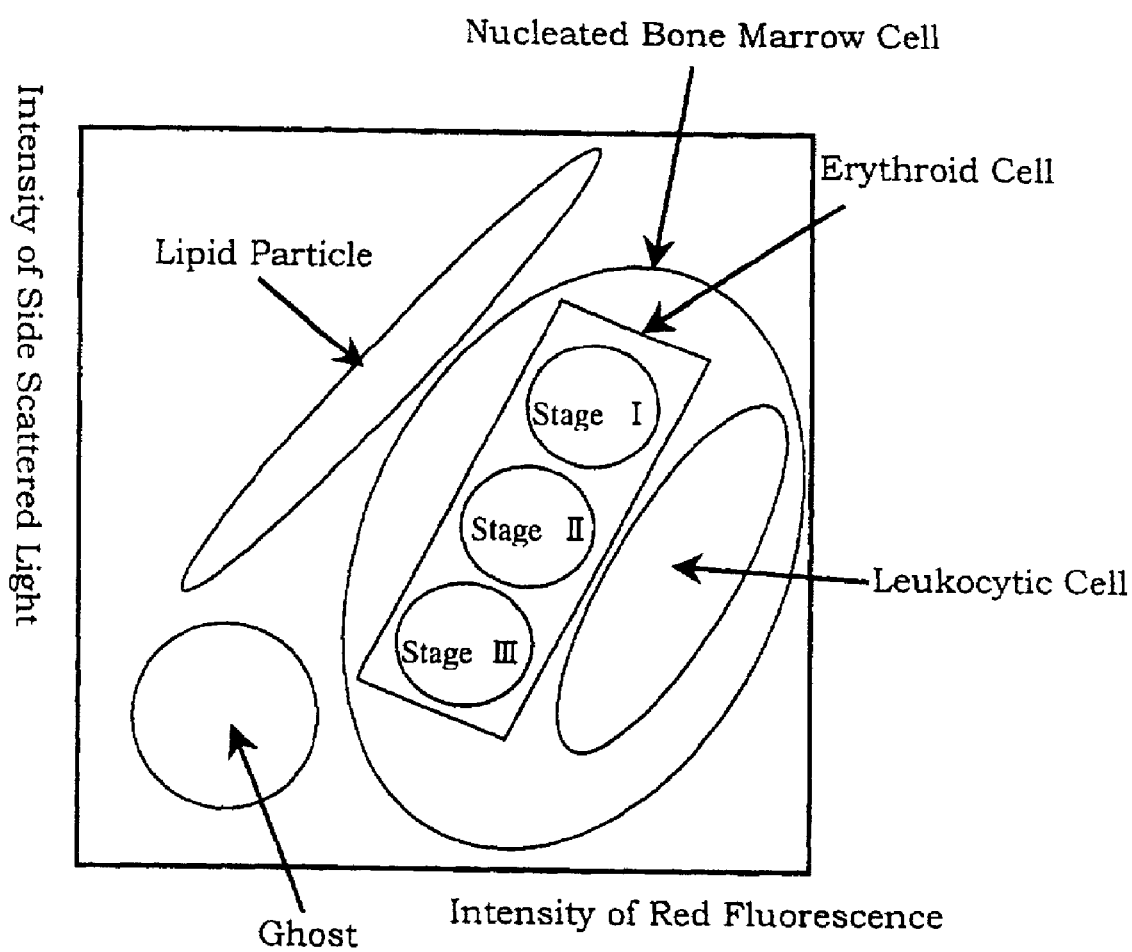
FIG. 1 schematically shows the distribution of components contained in bone marrow.

In the present invention, the sample of bone marrow fluid means a sample of bone marrow fluid including a bone marrow aspirate which contains leukocytic cells and erythroid cells of a mammal, especially a human. In the present invention, the sample of bone marrow fluid does not need particular pretreatment. However, if the presence of bone fragments or blood cell aggregates disturbs the measurement of leukocytic cells and erythroid cells, filtration may be carried out for removing bone fragments and aggregates as required. The sample of bone marrow fluid may be diluted with an aqueous solution containing an anticoagulant, a buffer or a chelating agent. As the anticoagulants used for anticoagulating the sample, usable are those usually used for blood tests such as heparin, citric acid, citrates and the like. As the buffer, a buffer as mentioned below may be used. As the chelating agent, EDTA salts and the like may be used. The sample may be diluted with the aqueous solution suitably about 5- to 100-fold (by volume), preferably about 10- to 50-fold.

In step (1), the sample of bone marrow fluid is mixed with the erythrocyte lysing agent. Thereby, erythrocytes contained in the sample are lysed to an extent such that they will not hinder the measurement of various kinds of component cells in bone marrow described later, and also leukocytic cells, erythroid cells and/or lipid particles are rendered suitable for staining. The erythrocyte lysing agent also makes pores in the cell membranes of erythroid cells and lyses the cells as the agent does to erythrocytes, but the condition of the cell nuclei of erythroid cells is substantially maintained as the condition of living cells. It is not clear what damage the erythrocyte lysing agent does to the cell membranes of leukocytic cells, but optical-microscopic observation reveals no remarkable difference from living cells and shows that leukocytic cells can be maintained substantially as the living cells.

The composition of the erythrocyte lysing agent is not particularly limited so long as the agent exhibits such action. At an osmotic pressure of 150 mOsm/kg or less, erythrocytes typically have pores in their cell membranes, from which intracellular hemoglobin flows out, and the erythrocytes become optically transparent (are lysed), though some difference is seen between individual cells. The optically transparent erythrocytes do not disturb the measurement of the component cells in the sample of bone marrow fluid any more. Erythrocytes are lysed more rapidly at a lower osmotic pressure and a lower pH. Accordingly, in the present invention, the erythrocyte lysing agent preferably has an osmotic pressure of 100 mOsm/kg or less, more preferably about 30 to 100 mOsm/kg, in consideration of difference between individual cells. If the pH is too low, the erythrocyte lysing agent does excessive damage not only to erythrocytes but also to leukocytic cells and erythroid cells, which reduces the below-described difference between the intensities of fluorescence from both leukocytic cells and erythroid cells. Therefore, the erythrocyte lysing agent suitably has an acid pH, preferably about 2.0 to 5.0, more preferably about 2.5 to 4.5.

In order to realize such an osmotic pressure and pH, the erythrocyte lysing agent is preferably an aqueous solution containing an electrolyte, a saccharide, a buffer and the like, for example. Further preferably, the agent contains an organic acid or its salt having at least one intramolecular aromatic ring since erythrocytes can be lysed more effectively (more rapidly). Also, the erythrocyte lysing agent preferably contains a surfactant.

As electrolytes, NaCl, KCl and the like may be mentioned. As saccharides monosaccharides, polysaccharides, oligosaccharides such as glucose, lactose, sucrose may be mentioned. As buffers, those having a pKa near pH ±2.0 to be set, and particular examples thereof include citric acid, malic acid, maleic acid, diglycolic acid, malonic acid or the like and salts thereof. As organic acids and their salts, salicylic acid, phthalic acid and the like, their alkali metal salts (e.g., sodium salts, potassium salts, etc.) and the like may be mentioned. These also act as buffers.

The concentration may be adjusted as appropriate depending upon the state of the sample of bone marrow fluid, the types and components of the erythrocyte lysing agent and the like, but may be about 0.1 to 100 mM, preferably about 1 to 30 mM.

The surfactant may be any surfactant so long as it can solubilize a slightly soluble dye, prevent erythrocyte ghosts from aggregation, preventing platelets from aggregation, shrink erythrocyte ghosts and/or promote erythrocyte lysis. For example, it is preferable to use the following surfactants singly or in combination of two or more thereof.

Compounds of Formula (A)

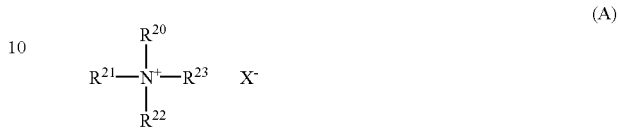

wherein, $R^{20}$, $R^{21}$ and $R^{22}$ are, the same or different, an hydrogen atom, a $C_{1-8}$ alkyl group or a $C_{6-8}$ aralkyl group; $R^{23}$ is a $C_{8-18}$ alkyl group, a $C_{8-18}$ alkenyl group or a $C_{5-18}$ aralkyl group; and $X^-$ is an anion, Compounds of Formula (B)

wherein $R^{24}$ is a $C_{8-18}$ alkyl group; and $X^-$ is an anion,

Compounds of Formula (C)

wherein $R^{25}$ and $R^{26}$ are, the same or different, a hydrogen atom, a $C_{1-8}$ alkyl group, or a $C_{6-8}$ aralkyl group; $R^{27}$ is a $C_{8-18}$ alkyl group, a $C_{8-18}$ alkenyl group or a $C_{6-18}$ aralkyl group; and n is 1 or 2, Compounds of Formula (D)

wherein $R^{28}$ is a $C_{9-25}$ alkyl group, a $C_{9-25}$ alkenyl group or a $C_{9-25}$ alkynyl group; $R^{29}$ is

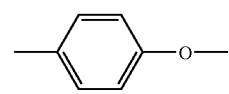

or —COO—; and n is an integer of 10 to 40,

-MEGA-8:

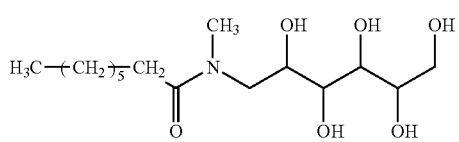

-sucrose monocaproate:
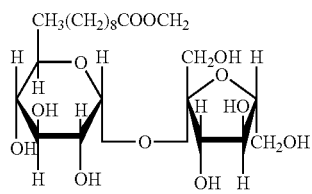
-Deoxy-BIGCHAP:
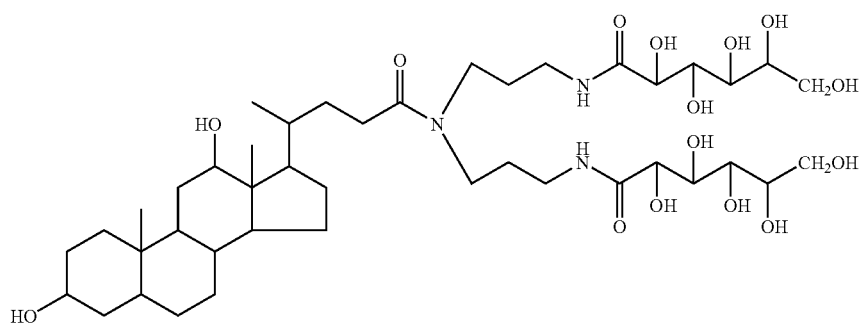
-n-octyl-β-D-thioglucoside:
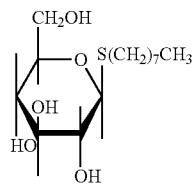
-n-nonyl-β-D-thiomaltoside:
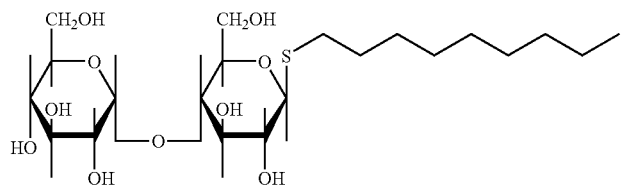
-n-heptyl-β-D-thioglucoside:
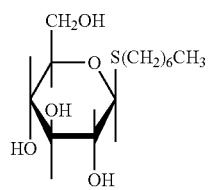
-n-octyl-D-oxyglucoside:
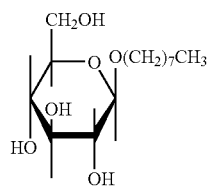

-CHAPS:

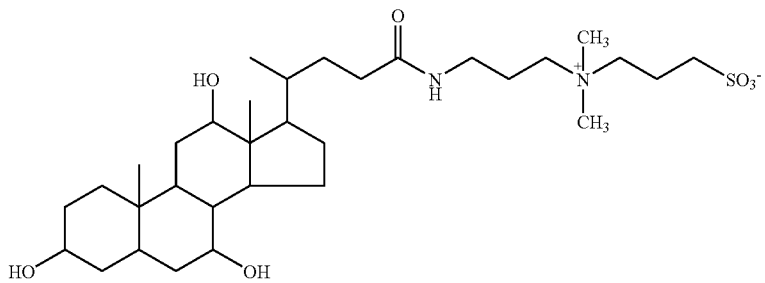

-CHAPSO:

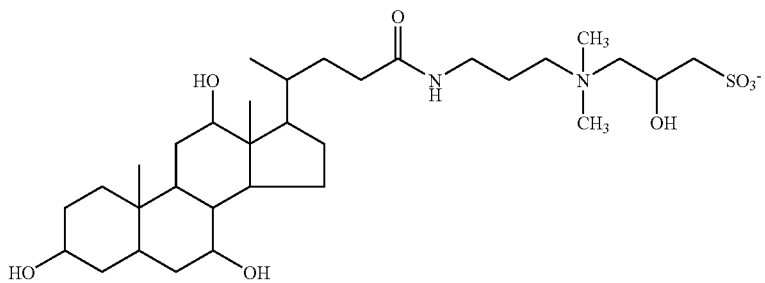

In the formulae, the $C_{1-8}$ alkyl group may be methyl, ethyl, propyl, t-butyl, n-butyl; isopentyl, neopentyl, t-pentyl, isohexyl, heptyl, octyl or the like, among which $C_{1-3}$ alkyl groups are preferred.

The $C_{6-8}$ aralkyl group may be benzyl, phenethyl or the like.

The $C_{8-18}$ alkyl group may be octyl, decyl, dodecyl, tetradecyl, oleyl or the like, among which $C_{10-18}$ straight-chain alkyl groups such as decyl, dodecyl, tetradecyl and the like are preferred.

The $C_{8-18}$ alkenyl group may be octenyl, decenyl, dodecenyl, tetradecenyl or the like.

The $C_{6-18}$ aralkyl group may be phenylpropylene, phenylbutene, naphthylmethylene, naphthylethylene, naphthylpropylene, biphenylmethylene, biphenylethylene or the like in addition to the above-mentioned aralkyl groups.

The $C_{9-25}$ alkyl group may be icosyl, henicosyl, docosyl, tricosyl or the like in addition to the above-mentioned alkyl groups.

The $C_{9-25}$ alkenyl group may be icosenyl, henicosenyl or the like in addition to the above-mentioned alkenyl groups.

The $C_{9-25}$ alkynyl group may be icosynyl, henicosynyl or the like.

Of the above-mentioned surfactants, those of Formulae E to M, i.e., MEGA-8 to CHAPSO, can be purchased from Kabushiki Kaisha Dojin Kagaku Kenkyusho, Japan.

The concentration of a surfactant used can be set as appropriate dependent upon the kind of the surfactant and the kind and concentration of the erythrocyte lysing agent used. Usually, if the concentration of the surfactant is too high, not only erythrocytes but also leukocytic cells and erythroid cells are excessively damaged. The shape of erythroid cells, in particular, is changed, which results in reduced differences in the intensity of fluorescence among erythroid cells, leukocytic cells and the lipid particles.

Therefore, the concentration of the surfactant is preferably about 10 to 10,000 mg/L, more preferably about 100 to 5,000 mg/L, further more preferably about 1,000 to 3,000 mg/L. It is noted that this concentration is the concentration of the surfactant in the erythrocyte lysing agent, The sample of bone marrow fluid may be mixed with the erythrocyte lysing agent suitably at 15 to 50° C., preferably at 20 to 40° C., suitably for 3 to 120 seconds, preferably for 5 to 40 seconds.

The sample of bone marrow fluid is stained with a fluorescent dye. It is necessary to use a fluorescent dye that can produce differences in the intensity of fluorescence at least among leukocytic cells and erythroid cells, preferably at least among leukocytic cells, erythroid cells and the lipid particles. Such a fluorescent dye, for example, may be one or two or more selected from the following groups:

Compounds of Formula (1)

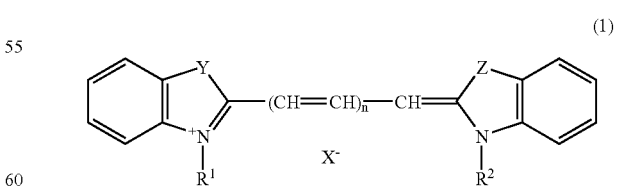

wherein $R^1$ and $R^2$ are, the same or different, a hydrogen atom, or an alkyl or alkenyl group optionally substituted by a hydroxyl group; Y and X are, the same or different, a hetero atom or a carbon atom substituted by a lower alkyl group; n is 0, 1 or 2; and $X^-$ is an anion, Compounds of Formula (2)

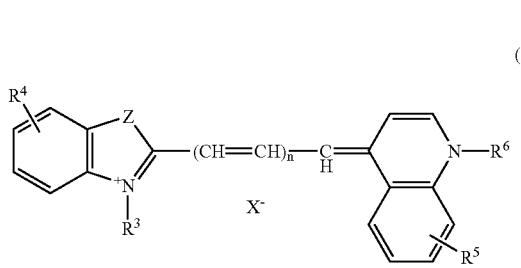

(2)

wherein $R^3$ is a hydrogen atom or an alkyl group; $R^4$ and $R^5$ are, the same or different, a hydrogen atom, a lower alkyl group or a lower alkoxy group; $R^6$ is a hydrogen atom, an acyl group or an alkyl group; Z is a hetero atom or a carbon atom substituted by a lower alkyl group; n is 0, 1 or 2; and $X^-$ is an anion, Compounds of Formula (3)

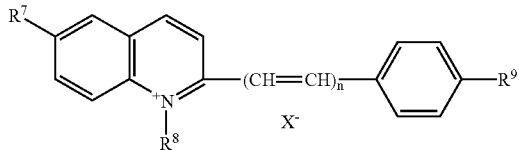

(3)

wherein $R^7$ is a hydrogen atom or a dimethylamino group; $R^8$ is an alkyl group; $R^9$ is a hydrogen group or a dimethylamino group; n is 1 or 2; and $X^-$ is an anion, Compounds of Formula (4)

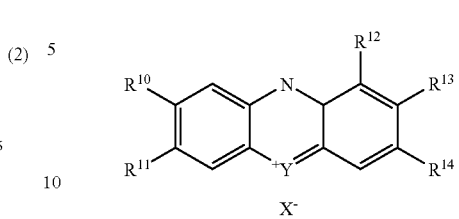

(4)

wherein $R^{10}$ is a hydrogen atom or an alkyl group; $R^{11}$ is a dimethylamino group; $R^{12}$ is a hydrogen atom or an amino group; $R^{13}$ is a hydrogen atom, an alkyl group or an amino group; $R^{14}$ is a hydrogen atom or a dimethylamino group; $X^-$ is an anion; and Y is a hetero atom, Compounds of Formula (5)

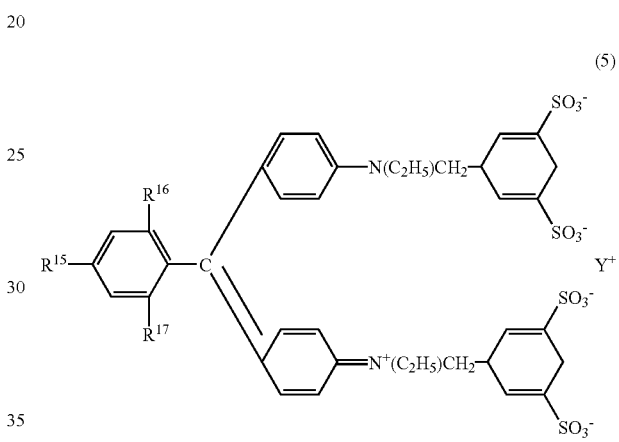

(5)

wherein $R^{15}$ is a hydrogen atom or a hydroxyl group; $R^{16}$ is a hydrogen atom or a sulfonic group; $R^{17}$ is a hydrogen atom or a sulfonic group; and Y is a cation,

-NK-2825:

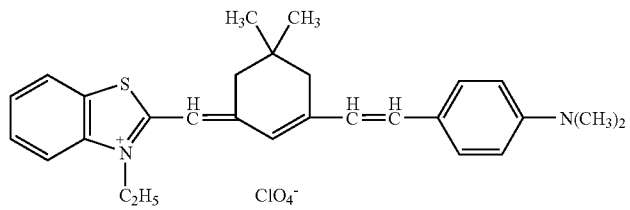

-NK-1836:

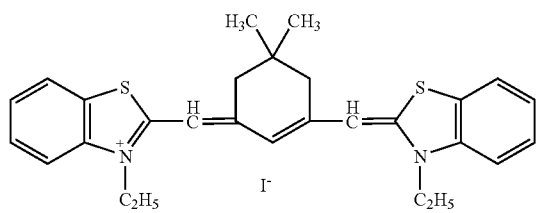

-NK-1954:
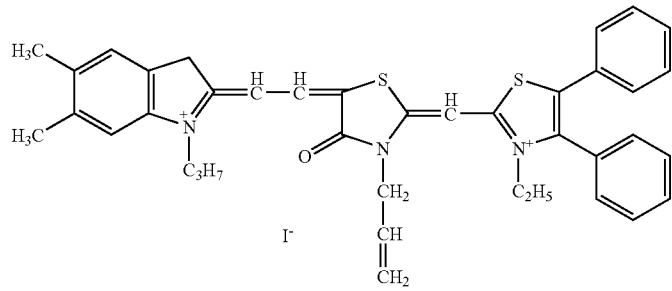
-Oxazine750:
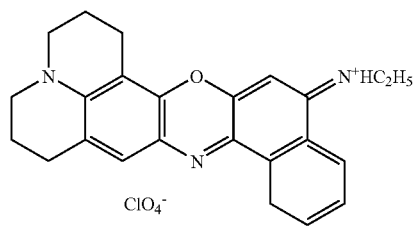
-Cryptocyanine:
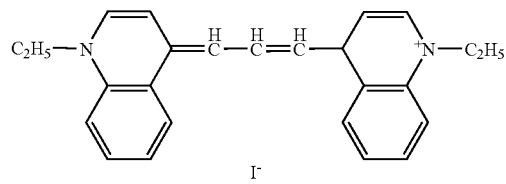
-NK-376:
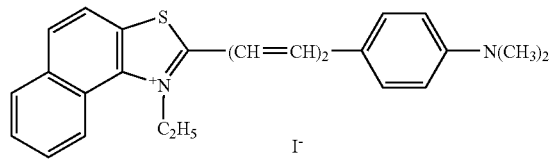
-NK-382:
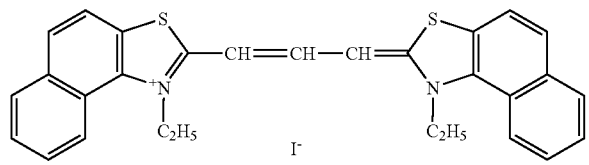
-NK-2711:
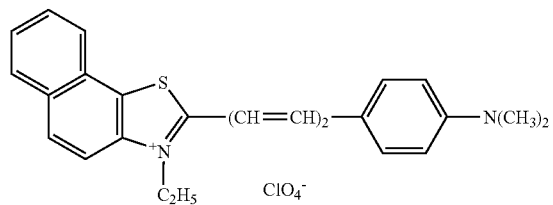
-NK-138:
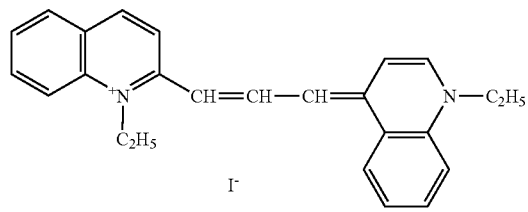

-continued
-Oxazine720:
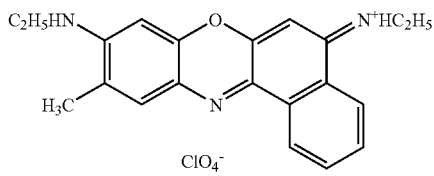
LDS730:
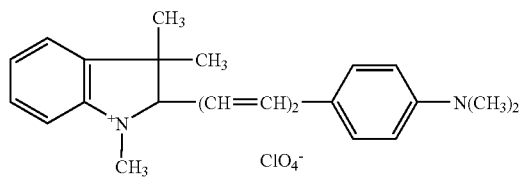
-LD700:
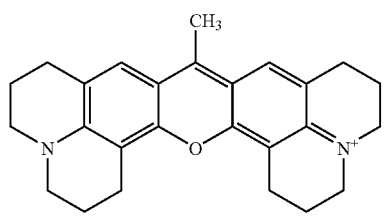
-Nile Blue A:
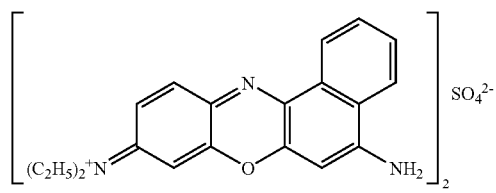
-Brilliant Green:
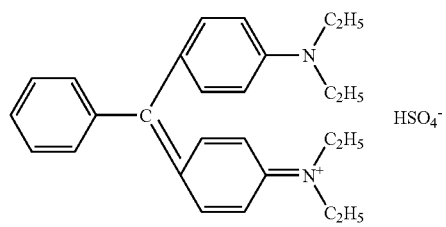
-Iodide green:
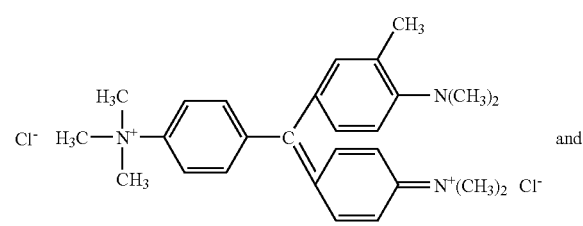
-Malachite green:
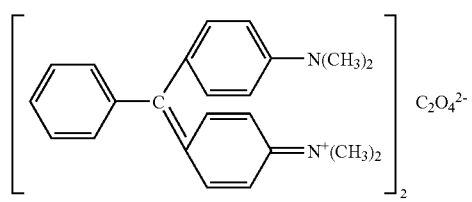

In the above formulae, alkyl groups bound to nitrogen atoms or carbon atoms of heterocycles are straight-chain or branched alkyl groups having 1 to 20, preferably 1 to 10, more preferably 1 to 6 carbon atoms) including methyl, ethyl, propyl, t-butyl, n-butyl, n-pentyl, n-hexyl and the like, for example.

The lower alkyl group means a straight-chain or branched all group having 1 to 8 carbon atoms, and examples thereof include methyl, ethyl and the like.

The lower alkoxy group means a straight-chain or branched alkoxy group having 1 to 8 carbon atoms, and examples thereof include methoxy, ethoxy and the like.

As acyl groups, may be mentioned those having 1 to 3 carbon atoms, including formyl, acetyl, propionyl and the like.

As anions, may be mentioned halogen ions such as $F^-$, $Cl^-$, $Br^-$ and $I^-$, $CF_3SO_3^-$, $BF_4^-$, $ClO_4^-$ and the like.

As hetero atoms, may be mentioned a nitrogen atom, a sulfur atom, an oxygen atom and the like.

As cations, may be mentioned $Na^+$, $K^+$, $Li^+$ and the like.

Of the above-mentioned dyes, the NK series can be purchased from Nippon Kanko Shikiso Kenkyusho Kabushiki Kaisha, Japan, LDS730 and LD700 can be purchased from Exciton Company, and the others are commercially available.

The fluorescent dye may be dissolved in the erythrocyte lysing agent and/or the surfactant and allowed to act on (mixed with) the sample of bone marrow fluid simultaneously when the erythrocyte lysing agent and/or the surfactant is/are mixed with the sample. Or alternatively, the fluorescent dye may be dissolved in a proper solvent (e.g., water, a lower alcohol, ethylene glycol, DMSO, etc.) and allowed to act on the sample, after the step of lysing erythrocytes.

The concentration of a dye used may vary depending upon the kind of the dye, but may be generally 0.01 to 100 mg/L, preferably 0.1 to 10 mg/L, more preferably 0.3 to 3.0 mg/L. This concentration of the fluorescent dye is a concentration in a mixture of the sample, the erythrocyte lysing agent and the fluorescent dye.

By this staining, leukocytic cells are strongly stained and emit fluorescence with strong intensity. Erythroid cells are weakly stained and emit fluorescence with weak intensity, Lipid particles, if contained, are also weakly stained and emit fluorescence with weak intensity. The mechanism of producing a difference in the intensity of fluorescence between leukocytic cells and erythroid cells is not clearly known. However, probably, since the nuclei (DNAs) of erythroid cells shrink, the dye is hindered from being taken into the nuclei of the cells.

In step (2), the resulting sample is introduced to a flow cytometer, and at least one kind of fluorescence and at least one kind of scattered light are measured. As the flow cytometer, any commercially available one can be used.

In the present invention, the scattered light means scattered light that can be measured by a commercially available flow cytometer, and includes forward low-angle scattered light (0° to 5° or smaller as an example of incident light angle), forward high-angle scattered light (50 to about 20° as an example of incident light angle) and side scattered light (about 90° as an example of incident light angle) Preferably, the side scattered light is selected, which reflects intracellular information such as the nuclear form of cells.

The fluorescence is emitted from the aforesaid dye having stained the cells. A suitable wavelength is selected to be detected according to the used dye. Fluorescent signals reflect chemical properties of the cells.

The light source of the flow cytometer is not particularly limited, but one having a wavelength suitable for exciting the dye is selected. For example, an argon ion laser, a He—Ne laser, a red semiconductor laser or the like may be used. The semiconductor laser, especially, is far less expensive than gas lasers and can contribute to a great reduction in the cost of the flow cytometer.

In Step (3), the nucleated bone marrow cells, erythroid cells and leukocytic cells (as well as the lipid particles) in the sample are classified and counted using differences in the intensity of the measured scattered light and fluorescence.

For classifying and counting the nucleated bone marrow cells using the differences in the intensity of the scattered light and fluorescence, for example, a scattergram is produced with the intensity of the fluorescence and that of the side scattered light in the abscissa and the ordinate, respectively. As shown in FIG. 1, the nucleated bone marrow cells, lipid particles and ghost cells are distributed to form their respective clusters. Next, using an appropriate analysis software, a region is set for each cluster and cells in the cluster are counted. Thereby, it is possible to classify and count the nucleated bone marrow cells as well as the lipid particles, erythroid cells and leukocytic cells.

In the case where there is little influence of lipid particles, erythroid cells, leukocytic cells and ghost cells are distributed to form their respective clusters, as shown in FIG. 1, on a scattergram which is produced with the intensity of fluorescence and the intensity of forward scattered light plotted in abscissa and ordinate, respectively, for example. Then, using an appropriate analysis software, a region is set for each cluster and cells in the cluster are counted. Thereby, it is possible to calculate the erythroid cell count and its ratio. Similarly, the leukocytic cell count can be calculated.

From the obtained nucleated bone marrow cell count and erythroid cell count or leukocytic cell count, it is possible to calculate the ratio of the nucleated bone marrow cells to the erythroid cells or leukocytic cells. Also, from the erythroid cell count and the leukocytic cell count, it is possible to calculate the ratio of the leukocytic cells to the erythroid cells.

Further, according to the present invention, subsequently to steps (1) to (3), the erythroid cells may be classified into at least two groups according to their degree of maturity using the differences in the intensity of the scattered light and fluorescence and the number of cells in each group may be counted. For classifying and counting the erythroid cells according to their degree of maturity, a scattergram is produced substantially in the same manner as described above, a region is set for each group according to the degree of maturity, and cells in the region are counted.

Thereby, it is possible to calculate the of erythroblasts at each degree of maturity to all the erythroid cells from the erythroid cell count at each degree of maturity and the total erythroid cell count.

Furthermore, according to the present invention, subsequently to steps (1) to (3), a myeloid cell count may be calculated by deducting a lymphocyte count and a monocyte count from leukocytic cell count. For calculating the myeloid cell count, for example, the same sample is analyzed by another blood cell counter to obtain the lymphocyte count and the monocyte count, and the obtained lymphocyte count and monocyte count are deducted from the leukocytic cell count. Thereby it is possible to calculate the ratio of the myeloid cells to the erythroid cells (M/E ratio), The ratio of the leukocytic cells to the erythroid cells is usually 2:1 to 5:1, and the ratio of the myeloid cells to the erythroid cells is 1.5:1 to 3.3 1. Diseases such as leukemia change these ratios to change. These ratios are useful for diagnosing acute myelocytic leukemia (AML) and myelodysplastic syndrome (MDS). Therefore, by determining these ratios as time passes, it is possible to grasp the pathology of various kind of leukemia, to monitor treatment and others.

Further it is possible to grasp the state of erythropoiesis in bone marrow from the erythroid cell count in nucleated bone marrow cells.

The present invention is now described in detail by way of the following example. However, it should be construed that various changes and modifications may be made to the present invention and that the scope of the present invention is not limited to the example.

EXAMPLES

Example 1

A reagent having the following composition was prepared.

| | |
|---|---|
| Salicylic acid (commercially available) | 10 mM |
| NK-2825 (Nippon Kanko Shikiso Kenkyusho) | 0.3 mg/L |
| LTAC (dodecyltrimethylammonium chloride) (commercially available) | 0.3 g/L |
| Purified water | 1 liter |

Adjusted to pH 3.0 with NaOH (an osmotic pressure of 40 mOsM/Kg).

The above-mentioned reagent, 1.0 mL, was added to 30 µL of bone marrow fluid of a patient suffering acute myelocytic leukemia (AML) and allowed to react at 40° C. for 5 seconds. Thereafter, side scattered light and red fluorescence were measured by a flow cytometer. As a light source, a semiconductor laser of 633 nm was used, and fluorescence having a wavelength of 660 nm or more was measured.

Figure 2:
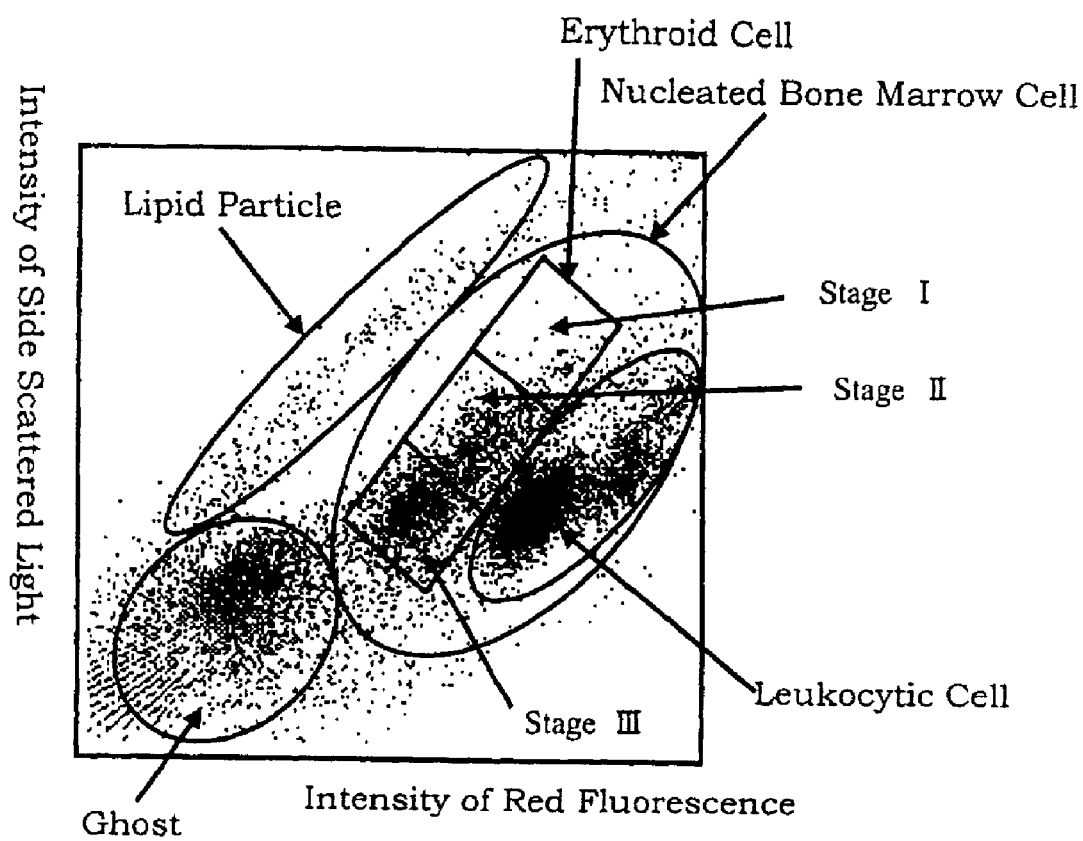
FIG. 2 is a scattergram showing the populations of cells in bone marrow with the intensity of red fluorescent and the intensity of side scattered light plotted in the abscissa and in the ordinate, respectively.
Figure 3:
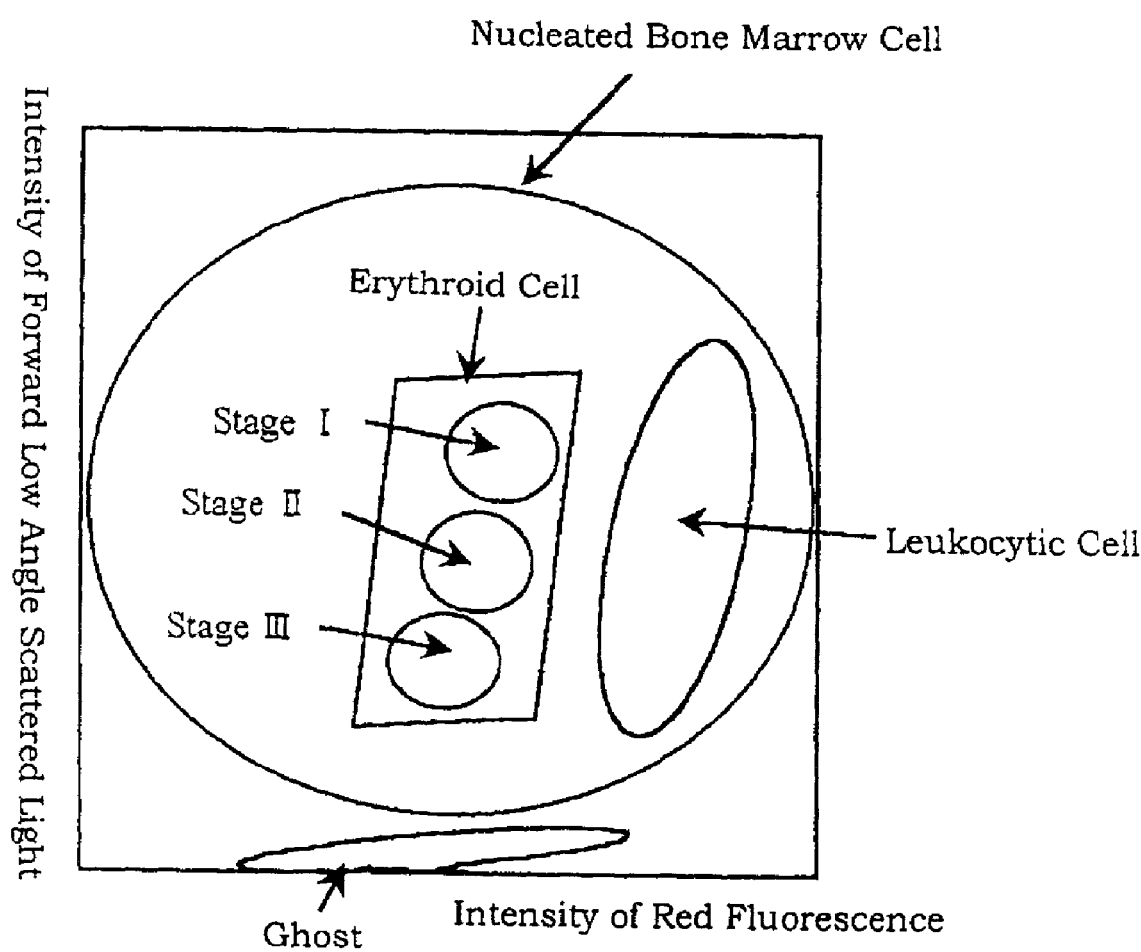
FIG. 3 schematically shows the distribution of components contained in bone marrow.

FIG. 2 is a scattergram with the intensity of red fluorescent and the intensity of side scattered light plotted in the abscissa and in the ordinate, respectively. Nucleated bone marrow cells form four clusters, i.e., of leukocytic cells, of erythroid cells in stage I, of erythroid cells in stage II and of erythroid cells in stage III.

The above bone marrow was subjected to May-Gruenwald's stain and then microscopically observed. The leukocytic cells and erythroid cells were classified, and the erythroid cells were further differentiated into proerythroblasts, basophilic erythroblasts, polychromatic erythroblasts and orthochromatic erythroblasts. Further, the myeloid cell count was calculated from the lymphocyte count and the monocyte count separately obtained by the blood cell counter. The ratio of the erythroid cells to the myeloid cells was calculated and compared with the aforesaid results obtained by the flow cytometer.

Table 1 shows the flow-cytometrically obtained results and the microscopically obtained results.

TABLE 1

| | Present Invention | Microscopic Observation |
|---|---|---|
| Nucleated bone marrow cell count (×10$^3$/µl) | 10250 | 9980 |
| Leukocytic cell count (×10$^3$/µl) | 9020 | 8800 |
| Erythroid cell count (×10$^3$/µl) | 1230 | 1180 |
| Nucleated bone marrow cell count:leukocytic cell count | 1.1:1 | 1.1:1 |
| Nucleated bone marrow cell count:erythroid cell count | 8.3:1 | 8.5:1 |
| Leukocytic cell count:erythroid cell count | 7.3:1 | 7.5:1 |
| Myeloid cell count:erythroid cell count (M/E ratio) | 6.1:1 | 5.9:1 |
| Erythroid cells in Stage I | 1.5% | 1% |
| Erythroid cells in Stage II | 25.7% | 26% |
| Erythroid cells in Stage III | 72.8% | 73% |

Table 1 shows that both the results agree considerably well with each other.

Example 2

The reagent of Example 1, 1.0 mL, was added to 30 µL of bone marrow fluid of a patient suffering acute myelocytic leukemia (AML) which contained few lipid particles, and allowed to react at 40° C. for 5 seconds. Thereafter, forward low-angle scattered light and fluorescence were measured by a flow cytometer. As a light source, a red semiconductor laser of 633 nm was used, and fluorescence having a wavelength of 660 nm or more was measured.

Figure 4:
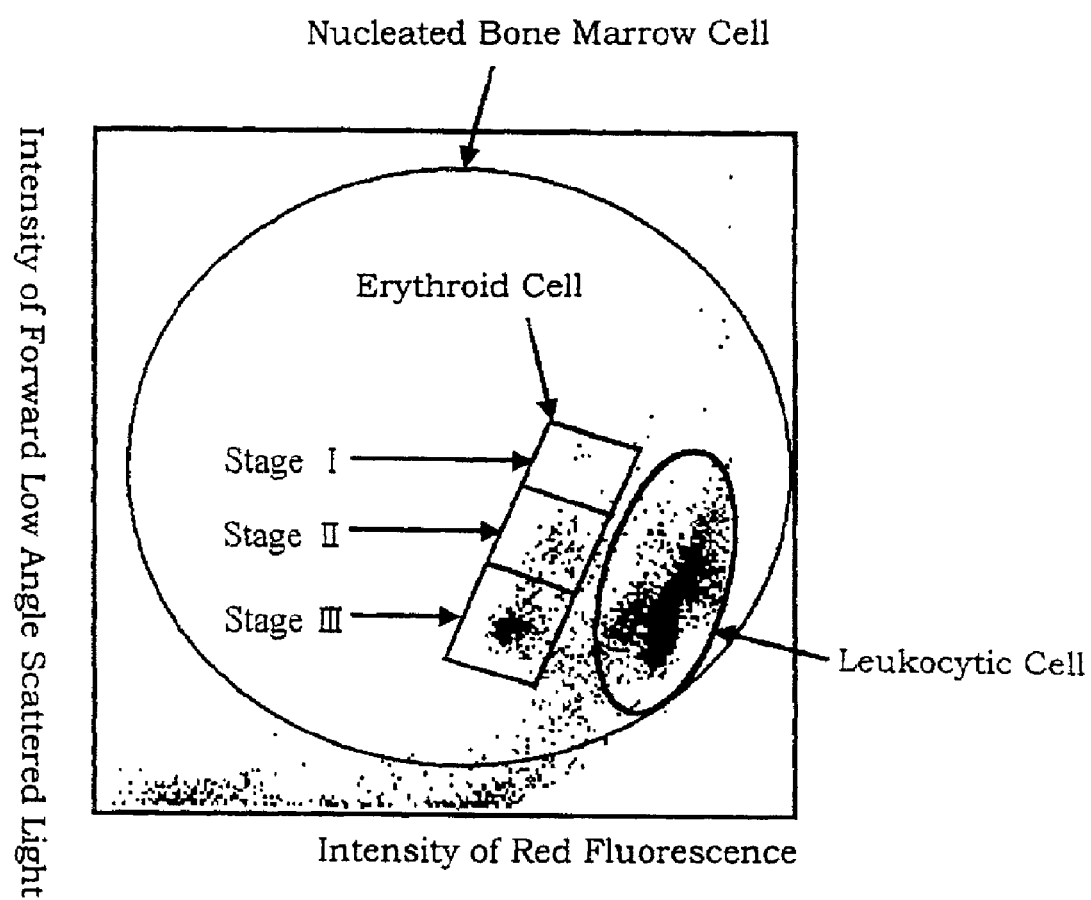
FIG. 4 is a scattergram showing the populations of cells in bone marrow with the intensity of red fluorescent and the intensity of forward scattered light plotted in the abscissa and in the ordinate, respectively.

FIG. 4 is a scattergram with the intensity of red fluorescent and the intensity of forward low-angle scattered light plotted in the abscissa and in the ordinate, respectively. Nucleated bone marrow cells form four clusters, i.e., of leukocytic cells, of erythroid cells in stage I, of erythroid cells in stage II and of erythroid cells in stage III.

The above bone marrow was subjected to May-Gruenwald's stain and then microscopically observed. The leukocytic cells and erythroid cells were classified, and the erythroid cells were further differentiated into proerythroblasts, basophilic erythroblasts, polychromatic erythroblasts and orthochromatic erythroblasts. Further, the myeloid cell count was calculated from the lymphocyte count and the monocyte count obtained by a blood cell counter. The ratio of the erythroid cells to the myeloid cells was calculated and compared with the aforesaid results obtained by the flow cytometer. Table 2 shows the flow-cytometrically obtained results and the microscopically obtained results.

TABLE 2

| | Present Invention | Microscopic Observation |
|---|---|---|
| Nucleated bone marrow cell count (×10$^3$/µl) | 1149 | 975 |
| Leukocytic cell count (×10$^3$/µl) | 1035 | 870 |
| Erythroid cell count (×10$^3$/µl) | 114 | 105 |
| Nucleated bone marrow cell count:leukocytic cell count | 1.11:1 | 1.12:1 |
| Nucleated bone marrow cell count:erythroid cell count | 10.1:1 | 9.29:1 |
| Leukocytic cell count:erythroid cell count | 9.1:1 | 8.29:1 |
| Myeloid cell count:erythroid cell count (M/E ratio) | 6.4:1 | 7.0:1 |
| Erythroid cells in Stage I | 0.5% | 0% |
| Erythroid cells in Stage II | 17.8% | 18% |
| Erythroid cells in Stage III | 81.7% | 82% |

Table 2 shows that both the results agree considerably well with each other.

Thus, unexpectedly, according to the present intention, it has become possible to produce clear differences in the intensity of scattered light and in the intensity of fluorescence between lipid particles and nucleated bone marrow cells, to produce a clear difference in the intensity of fluorescence between erythroid cells and leukocytic cells, thereby to classify and count nucleated bone marrow cells, erythroid cells and leukocytic cells, and further classify and count erythroid cells according to their degree of maturity.

It has also become possible to obtain the ratio of erythroid cells to nucleated bone marrow cells, the ratio of leukocytic cells to nucleated bone marrow cells and the ratio of erythroid cells to leukocytic cells. Besides, it has become possible to calculate the myeloid cell count and the ratio of erythroid cells to myeloid cells (the M/E ratio) by obtaining the lymphocyte count and the monocyte count by a blood cell counter.

What is claimed is:

1. A method of classifying and counting leukocytic cells and erythroid cells in a bone marrow fluid comprising leukocytic cells and erythroid cells and lipid particles comprising the steps of:
   (1) (a) mixing a sample of the bone marrow fluid with an erythrocyte lysing agent to lyse erythrocytes in the sample, thereby rendering leukocytic cells, erythroid cells and lipid particles in the sample suitable for staining, and
   (b) staining the sample with a fluorescent dye for producing a difference in intensity of fluorescence among the leukocytic cells, the erythroid cells, and the lipid particles;
   (2) introducing the resulting sample to a flow cytometer to detect at least one kind of scattered light and at least one kind of fluorescence;
   (3) classifying the lipid particles, the leukocytic cells and the erythroid cells by the difference in the intensities of their fluorescence and their scattered light; and
   (4) obtaining a count of the leukocytic cells and erythroid cells in the step of (3).

2. The method according to claim 1, further comprising the steps of:
   classifying erythroid cells into at least two erythroid cell groups according to maturity of each of the erythroid cells, and obtaining a count of cells in each of the erythroid cell groups by the difference in the intensities of the fluorescence and the scattered light from the at least two erythroid cell groups; and
   calculating the ratio of the classified cells in each of the erythroid cell groups to the total erythroid cell count.

3. The method according to claim 1, further comprising the steps of:
   classifying lymphocytes and monocytes included in the leukocytic cells and obtaining a lymphocyte count and a monocyte count; and
   calculating a myeloid cell count by deducting the obtained lymphocyte count and the obtained monocyte count from the leukocytic cell count; and
   calculating the ratio of the erythroid cells to myeloid cells from the obtained myeloid cell count and erythroid cell count.

4. The method according to claim 1, wherein the erythrocyte lysing agent is an aqueous solution having an osmotic pressure of 100 mOsm/kg or less and a pH of 2.0 to 5.0.

5. The method according to claim 1, wherein the fluorescent dye comprises one or more dyes selected from the group consisting of:
compounds of formula (1)

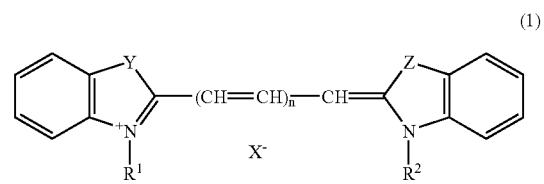

wherein $R^1$ and $R^2$ are, the same or different, a hydrogen atom, or an alkyl or alkenyl group optionally substituted by a hydroxyl group; Y and X are, the same or different, a hetero atom or a carbon atom substituted by a lower alkyl group; n is 0, 1 or 2; and $x^-$ is an anion,
compounds of formula (2)

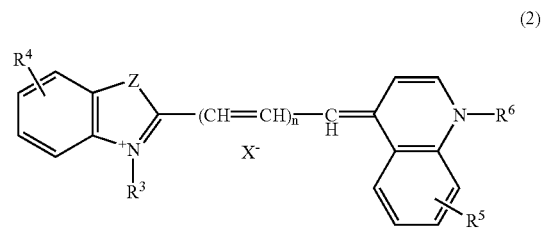

wherein $R^3$ is a hydrogen atom or an alkyl group; $R^4$ and $R^5$ are, the same or different, hydrogen atom, a lower alkyl group or a lower alkoxy group; $R^6$ is a hydrogen atom, an acyl group or an alkyl group; Z is a hereto atom or a carbon atom substituted by a lower alkyl group; n is 0, 1 or 2; and $x^-$ is an anion,
compounds of formula (3)

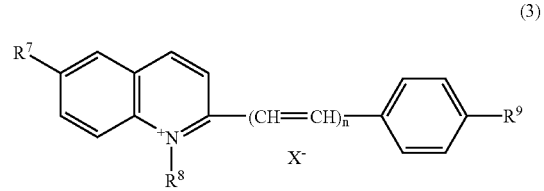

wherein $R^7$ is a hydrogen atom or a dimethylamino group; $R^8$ is an alkyl group; $R^9$ is a hydrogen group or a dimethylamino group; n is 1 or 2; and $x^-$ is an anion,
compunds of formula (4)

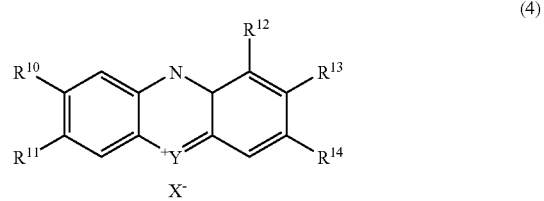

wherein $R^{10}$ is a hydrogen atom or an alkyl group; $R^{11}$ is a dimethylamino group; $R^{12}$ is a hydrogen atom or an amino group; $R^{13}$ is a hydrogen atom, an alkyl group or an amino group; $R^{14}$ is a hydrogen atom or a dimethylamino group; $X^-$ is an anion; and Y is a hetero atom, compounds of formula (5)

(5)

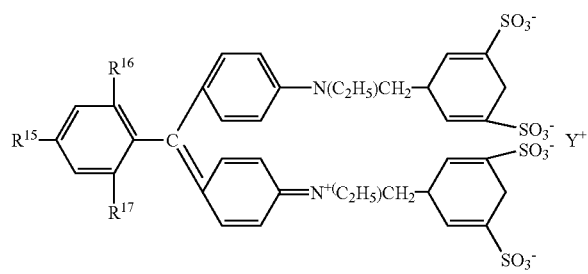

wherein $R^{15}$ is a hydrogen atom or a hydroxyl group; $R^{16}$ is a hydrogen atom or a sulfonic group; $R^{17}$ is a hydrogen atom or a sulfonic group; and Y is a cation,

-NK-2825:

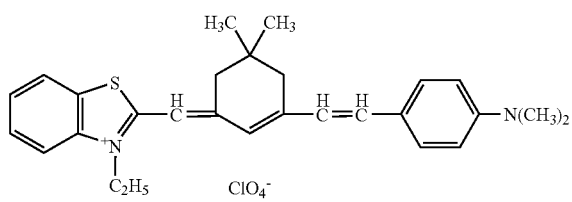

-NK-1836:

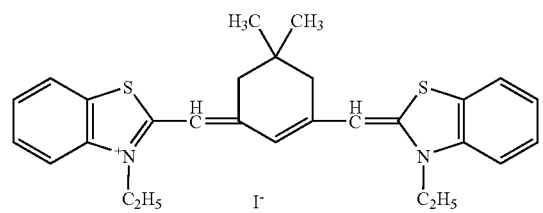

-NK-1954:

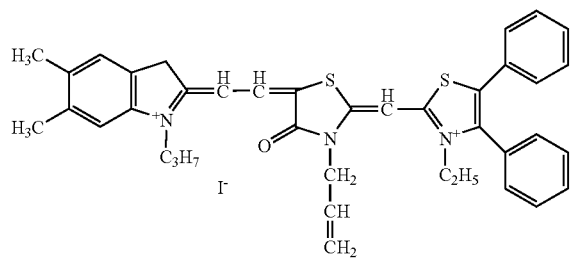

-Oxazine750:

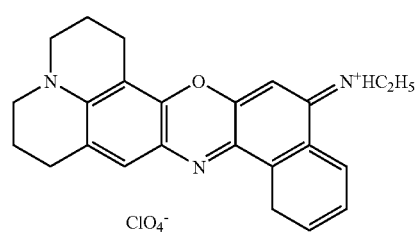

-Cryptocyanine:

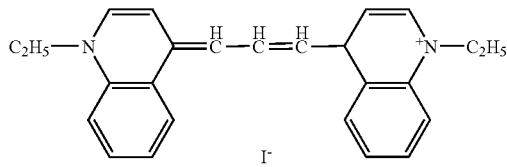

-NK-376:

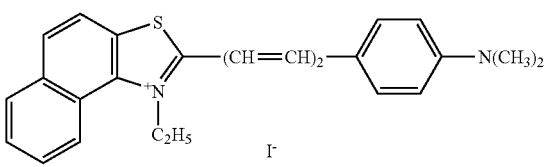

-NK-382:

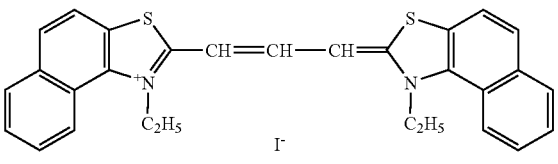

-NK-2711:

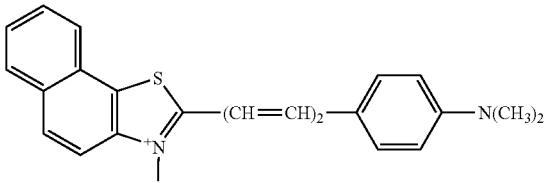

-NK-138:

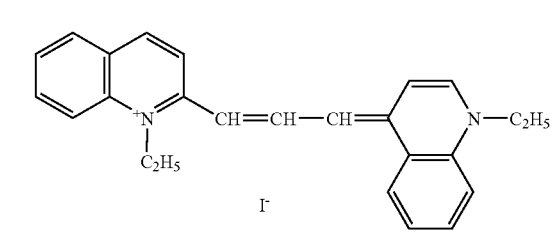

-Oxazine720:

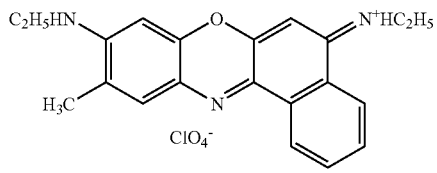

-LDS730:

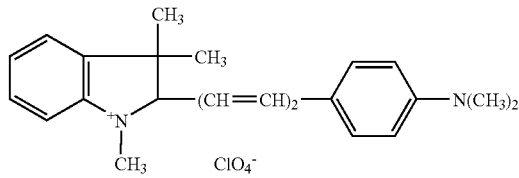

-continued

-LD700:

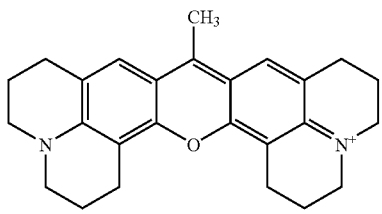

-Nile Blue A:

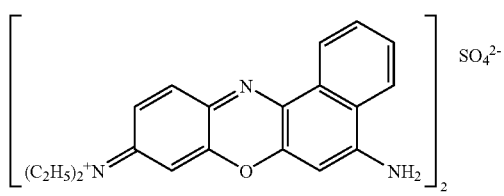

-Brilliant Green:

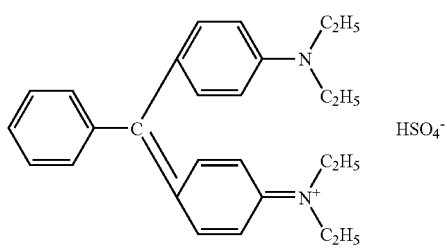

-Iodide green:

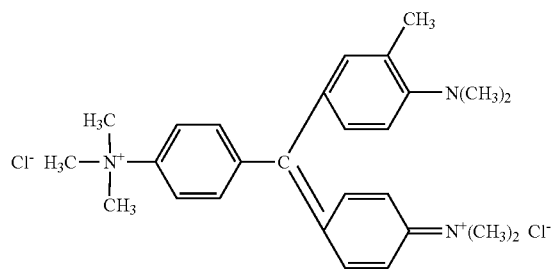

-Malachite green:

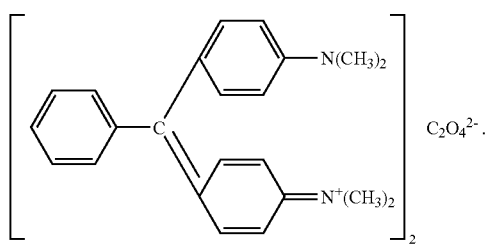

6. A method according to claim 1, wherein the erythrocyte lysing agent contains a surfactant, the surfactant comprises one or more surfactants selected from the group consisting of compounds of formula (A)

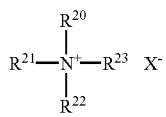

(A)

wherein $R^{10}$, $R^{21}$ and $R^{22}$ are, the same or different, an hydrogen atom, a $C_{1-8}$ alkyl group or a $C_{6-8}$ aralkyl group; $R^{23}$ is a $C_{8-18}$ alkyl group, a $C_{8-18}$ alkenyl group or a $C_{6-18}$ alkenyl group or a $C_{6-18}$ aralkyl group; and $X^-$ is an anion, compounds of formula (B)

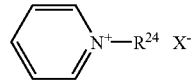

(B)

wherein $R_{24}$ is a $C^{8-18}$ alkyl group; and $X^-$ is an anion, compounds of formula (c)

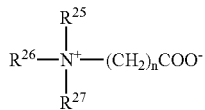

(C)

wherein $R^{25}$ and $R^{26}$ are, the same or different, a hydrogen atom, a $C_{1-8}$ alkyl group, or a $C_{6-8}$ aralkyl group; $R^{27}$ is a $C_{8-18}$ alkyl group, a $C_{8-18}$ alkenyl group or a $C_{8-18}$ aralkyl group; and n is 1 or 2, compounds of formula (D)

wherein $R^{25}$ and $R^{26}$ are, the same or different, a hydrogen atom, a $C_{1-8}$ alkyl group, or a $C_{6-8}$ aralkyl group; $R^{27}$ is a $C_{8-18}$ alkyl group, a $C_{8-18}$ alkenyl group or a $C_{6-16}$ aralkyl group; and n is 1 or 2, compounds of formula (D)

$$R^{28}-R^{29}-(CH_2CH_2O)\,n-H \quad (D)$$

wherein $R^{28}$ is a $C_{9-25}$ alkyl group, a $C_{9-25}$ alkenyl group or a $C_{9-25}$ alkynyl group; $R^{29}$ is

or —COO—; and n is an integer of 10 to 40,

-MEGA-8:
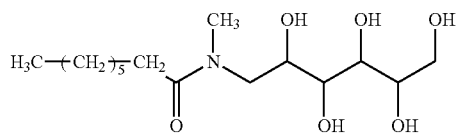
-sucrose monocaproate:
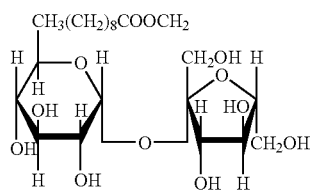
-Deoxy-BIGCHAP:
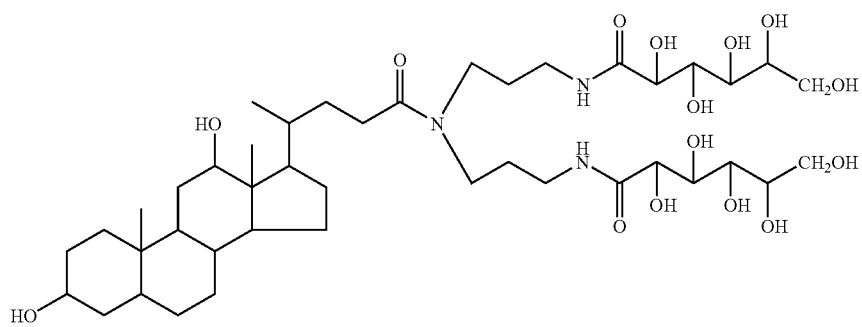
-n-octyl-β-D-thioglucoside:
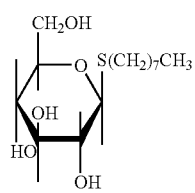
-n-nonyl-β-D-thiomaltoside:
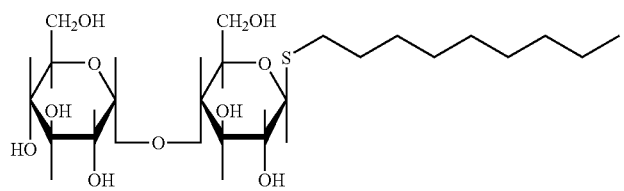
-n-heptyl-β-D-thioglucoside:
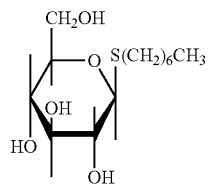
-n-octyl-D-oxyglucoside:
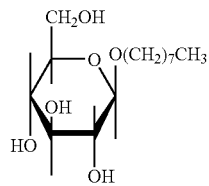

-CHAPS:

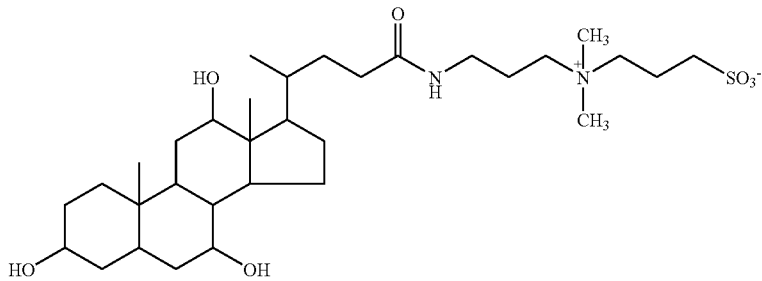

-CHAPSO:

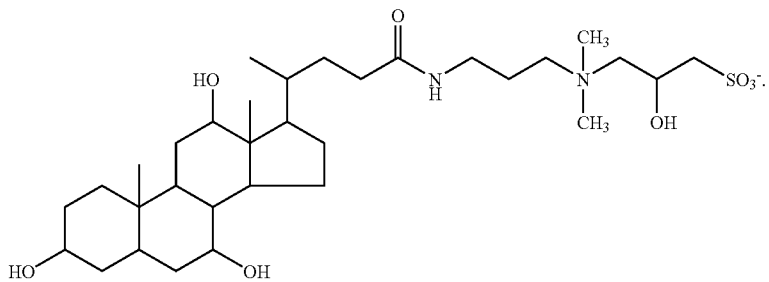

7. The method according to claim 6, wherein the concentration of the surfactant is 10 to 10000 mg/L.

8. The method according to claim 1, wherein the detected scattered light is one or more kinds of scattered light selected from the group consisting of forward low-angle scattered light, forward high-angle scattered light and side scattered light.

9. The method according to claim 1 further comprising the step of:
calculating the ratio of the total count of leukocytic cells and erythroid cells to the count of erythroid or leukocytic cells.

10. The method according to claim 1, further comprising the step of:
calculating the ratio of the obtained leukocytic cell count to the obtained erythroid cell count.

11. A method of classifying and counting leukocytic cells and erythroid cells in a bone marrow fluid comprising leukocytic cells and erythroid cells and lipid particles comprising the steps of:

(1) (a) mixing a sample of the bone marrow fluid with an erythrocyte lysing agent to lyse erythrocytes in the sample, thereby rendering leukocytic cells, erythroid cells and lipid particles in the sample suitable for staining, and
(b) staining the sample with a fluorescent dye for producing a difference in intensity of fluorescence among the leukocytic cells, the erythroid cells, and the lipid particles;

(2) introducing the resulting sample to a flow cytometer to detect side scattered light and at least one kind of fluorescence;

(3) classifying the lipid particles, the leukocytic cells and the erythroid cells by the difference in the intensities of their fluorescence and their scattered light; and (4) obtaining a count of the leukocytic cells and erythroid cells in the step of (3).

* * * * *